US012644797B2

(12) United States Patent
Higgins et al.

(10) Patent No.: US 12,644,797 B2
(45) Date of Patent: Jun. 2, 2026

(54) TISSUE SAMPLING KIT

(71) Applicant: IDENTIGEN LIMITED, Dublin (IE)

(72) Inventors: Mari Janika Higgins, Dublin (IE); David Thomas, Dublin (IE)

(73) Assignee: IDENTIGEN LIMITED, Dublin (IE)

( * ) Notice: Subject to any disclaimer, the term of this patent is extended or adjusted under 35 U.S.C. 154(b) by 915 days.

(21) Appl. No.: 17/792,046

(22) PCT Filed: Jan. 8, 2021

(86) PCT No.: PCT/EP2021/050254
§ 371 (c)(1),
(2) Date: Jul. 11, 2022

(87) PCT Pub. No.: WO2021/140191
PCT Pub. Date: Jul. 15, 2021

(65) Prior Publication Data
US 2023/0143077 A1 May 11, 2023

(30) Foreign Application Priority Data

Jan. 10, 2020 (GB) ...................................... 2000385

(51) Int. Cl.
*G01N 1/08* (2006.01)
*A22C 17/00* (2006.01)
(Continued)

(52) U.S. Cl.
CPC .............. *G01N 1/08* (2013.01); *A22C 17/00* (2013.01); *A61B 10/02* (2013.01); *B01L 3/5085* (2013.01);
(Continued)

(58) Field of Classification Search
CPC .... G01N 1/08; G01N 35/0099; G01N 35/026; G01N 35/10; G01N 2035/1032;
(Continued)

(56) References Cited

U.S. PATENT DOCUMENTS 4,707,450 A 11/1987 Nason
2011/0087133 A1* 4/2011 Ching .................... A61B 10/02
600/572

(Continued)

FOREIGN PATENT DOCUMENTS

EP 0295349 A2 12/1988
WO 2008034847 A1 3/2008
WO 2016091868 A1 6/2016

OTHER PUBLICATIONS

Canadian Office Action and Search Report dated Nov. 2, 2023 for corresponding Canadian Application No. 3,162,596.
(Continued)

*Primary Examiner* — Charles Capozzi
*Assistant Examiner* — Jacqueline Brazin
(74) *Attorney, Agent, or Firm* — Keith O'Doherty

(57) ABSTRACT

A sampling kit for tissue including a reaction chamber and a sampling device configured for mounting in the reaction chamber and providing a reaction volume defined between the base of the reaction chamber and the sampling device. The sampling device has a proximal handling portion and a distal scraping portion comprising a scraping formation configured to collect a sample of tissue when the distal scraping portion is rubbed against a surface of the tissue. The sampling device comprises an internal lumen configured for the supply of reaction liquid from a distal end of the tissue sampling device to the reaction volume via a distal aperture disposed in the distal scraping portion when the tissue sampling device is mounted in the reaction chamber. An automated high-throughput sampling and indexing system is also described.

12 Claims, 6 Drawing Sheets

(51) Int. Cl.
*A61B 10/02* (2006.01)
*B01L 3/00* (2006.01)
(52) U.S. Cl.
CPC ..... *B01L 2200/02* (2013.01); *B01L 2300/047* (2013.01); *B01L 2300/0829* (2013.01)
(58) Field of Classification Search
CPC .. G01N 35/00732; A22C 17/00; A61B 10/02; A61B 10/0233; B01L 3/5085; B01L 2200/02; B01L 2300/047; B01L 2300/0829; B01L 3/5029; B01L 2300/021; B01L 2300/023; B01L 2400/0457; A22B 5/0064
USPC ....................................................... 435/309.1
See application file for complete search history.

(56) References Cited

U.S. PATENT DOCUMENTS

| | | | |
|---|---|---|---|
| 2011/0146419 A1* | 6/2011 | Gonzalez | A61B 10/0045 |
| | | | 73/864.11 |
| 2017/0232437 A1 | 8/2017 | Butts et al. | |
| 2018/0126343 A1 | 5/2018 | Wiles et al. | |

OTHER PUBLICATIONS

International Search Report dated Apr. 23, 2021 for corresponding International Application No. PCT/EP2021/050254, Jan. 8, 2021.
Written Opinion of the International Searching Authority dated Apr. 23, 2021 for corresponding International Application No. PCT/EP2021/050254, filed Jan. 8, 2021.
Invitation to Pay Additional Fees dated May 4, 2021 for corresponding International Application No. PCT/EP2021/050254, filed Jan. 8, 2021.
British Search Report dated May 5, 2020 for corresponding Great Britain Application No. 2000385.1.
Bybee et al., "Targeted Amplicon Sequencing (TAS): A Scalable Next-Gen Approach to Multilocus, Multitaxa Phylogenetics", Genome Biology and Evolution, 3: 1312-1323, doi: 10.1093/gbe/evr106, PMC 3236605, Oct. 2011.
Masser et al., "Targeted DNA Methylation Analysis by Next-generation Sequencing", Journal of Visualized Experiments, 96:52488, doi: 10.3791/52488, PMC 4354667, Feb. 2015.
Islam et al., "A Review on Macroscale and Microscale Cell Lysis Methods", Micromachines, Journal, 8(3):83), doi:10.3390/mi8030083, Mar. 2017.

* cited by examiner

TISSUE SAMPLING KIT

CROSS-REFERENCE TO RELATED APPLICATIONS

This Application is a Section 371 National Stage Application of International Application No. PCT/EP2021/050254, filed Jan. 8, 2021, which is incorporated by reference in its entirety and published as WO 2021/140191 A2 on Jul. 15, 2021, not in English.

FIELD OF THE INVENTION

The present invention relates to a sampling kit, for use with tissues such as meat carcasses used in the food industry. The invention also relates to method of tissue sampling.

BACKGROUND TO THE INVENTION

Tissue sampling kits are used in the meat industry to take a sample of tissue from a carcass, which sample can then be used to extract carcass-specific DNA which may be used to determine carcass-specific information, for example the source of the meat (i.e. country, herd, farm, abattoir), or to determine the source of a microbial pathogen. The uses of tissue sampling kits, and a specific tissue sampling kit is described in WO2008/034847 (Parlanca Limited). The kit comprises a tissue sampling device, and a cap for receiving the device after a sampling operation. The sampling device has a handle portion and a sampling portion having a scraping edge for scraping tissue from a carcass. The scraping portion is provided by a series of deep circumferential edges to rip tissue from the carcass (as opposed to scraping a few meat fibres). After a tissue sampling operation, the cap is placed on the device to protect the tissue sampling portion of the device from contamination during transport to a laboratory. In the laboratory the cap is removed, and tissue sampling portion is placed into a well of the multiwell plate that already contains reaction fluid. The device is designed to nest snugly and securely in the well. In the well, the reaction fluid reacts with the tissue to lyse cells and release DNA during an incubation period. After the incubation period, the device is removed from the well, and a sample of the liquid in the well containing free DNA is withdrawn for analysis. During this process, the retraction of the device from the well has been found to result in drops of the removed liquid falling on to the plate and contaminating other wells in the plate, leading to well contamination and corrupted analysis results.

U.S. Pat. No. 4,707,450 describes a specimen collection and test unit provided for use in collecting a biological specimen. The specimen collection and test unit comprise an elongated swab having a fibrous tip mounted at one end of an elongated hollow shank. The opposite end of the swab shank is carried by an enlarged, generally cylindrical hollow base formed from a plastic material or the like and having sufficient resiliency to permit manual squeezing and bending without significant plastic deformation. The cylindrical base contains one or more reagents preserved within one or more closed frangible ampoules.

In use, the swab and base are manually handled as a unit for collecting a biological specimen or the like on the fibrous tip of the swab, without removal of the swab from the cylindrical base. After the specimen is collected, the cylindrical base is manually bent or otherwise deformed to rupture the frangible ampoule or ampoules thereby releasing the reagents therein which can be suitably mixed by gentle shaking of the base. The reagents are thereupon available for pumping through the hollow swab shank to the fibrous tip by application of manual pressure to the cylindrical base.

Once incubated, the test unit has to be removed from a reagent chamber to allow the fluid in the chamber to be sampled, thereby exposing the chamber and the system to cross-contamination.

It is an object of the invention to overcome at least one of the above-referenced problems.

SUMMARY OF THE INVENTION

The Applicant has addressed the problems of the prior art by providing a sampling device or a kit comprising a sampling device and a reaction chamber (for example a well or a cap), where the sampling device has a through lumen that allows fluid to be added to the reaction chamber, or withdrawn from the reaction chamber, using one or more apertures while the tissue sampling device is nested in the reaction chamber. The through lumen generally extends from a top (proximal) aperture to one or more apertures disposed in the sampling (distal) portion of the device. In use, the sampling device containing scraped tissue can be nested snugly in the well of a multiwell plate (or an individual well provided by a cap), and the reaction liquid then added to the well through the lumen of the sampling device. In this way, the reaction liquid can be inserted only after the sampling device is mounted into the reaction chamber, thus limiting the risk of spilling. Importantly, the provision of a sampling device having an internal lumen allows for liquid to be withdrawn from the well through the lumen, without having to remove the sampling device from the well, thereby addressing the problems of contamination associated with the devices of the prior art. The kit of the invention can take two forms, one in which the reaction chamber is the well of a multiwell plate (FIGS. 1-3B and 7), and another in which the reaction chamber is provided by a cap into which the sampling device is mounted (FIGS. 4A-6). The cap may be configured for detachable mounting to the distal scraping portion of the device (to act as a reaction chamber), but also for detachable mounting to the proximal handling portion of the device, to act as an handle extension for ease of use during a sampling operation. The invention also provides, as set out below, an automated tissue sampling system comprising a robotic arm.

In a first aspect, the invention provides a sampling kit comprising a reaction chamber and a sampling device configured for mounting in the reaction chamber and providing a reaction volume defined between the base of the reaction chamber and the sampling device, the sampling device having a proximal handling portion and a distal scraping portion comprising a scraping formation configured to collect a sample of tissue when the distal scraping portion is rubbed against a surface of the tissue. The kit is characterised in that the sampling device generally comprises an internal lumen configured for the supply of reaction liquid from a distal end of the sampling device to the reaction volume via a distal aperture (for example a window or slot) disposed in the distal scraping portion when the sampling device is mounted in the reaction chamber.

Such sample of tissue is for example meat tissue fibres. The scraping formation according to the disclosure is thus suitable to collect meat tissue fibres.

In one embodiment, the reaction chamber comprises a cap for the tissue sampling device.

In one embodiment, the cap is configured to detachably attach to the proximal handling end of the tissue sampling device to provide a handling extension.

In one embodiment, an external base of the cap includes an electronic identification tag readable by a flat-bed scanner. The tag may be, for example, an RFID tag or a barcode.

In another embodiment, the reaction chamber comprises a well of a multiwell plate.

In one embodiment, the sampling device is substantially hollow and provides an internal lumen extending from an open top to at least one aperture in a sidewall of the distal sampling portion.

In one embodiment, at least two distal apertures are provided in the sidewall of the distal sampling portion. The at least two apertures may be disposed on opposite sides of the device.

The internal lumen is typically configured to receive a pipette tip, a syringe or needle, or any suitable device that can be used for withdrawing liquid out of the reaction volume or pushing liquid into the reaction volume. This allows a pipette tip or any suitable device to be inserted into the lumen and extend through the lumen into reaction fluid in the lumen. It is thus possible to add liquid to the reaction chamber, and/or remove liquid from the reaction chamber through the lumen, thus enabling the digestion/solubilisation of the tissue, without removal of the sampling device from the well/cap. In other words, the internal lumen is both configured for the supply of reaction liquid and for the subsequent withdrawal of the reaction liquid mixed with the tissue sample (reaction mixture or a product produced by the reaction mixture) when the tissue sampling device is mounted in the reaction chamber (well or cap, where the cap can be placed in a well of a multiwell plate for example).

In one embodiment, the distal aperture in the distal sampling portion is disposed proximally of the scraping formation.

In one embodiment, the distal scraping portion comprises a conical end portion.

In one embodiment, the scraping formations comprises one or more fully or partially circumferential grooves. In one embodiment, the scraping formation has a depth of not more than 1 mm.

In one embodiment, the one or more fully or partially circumferential grooves are disposed in the conical end portion of the distal scraping portion. In one embodiment, the circumferential grooves have a depth of not more than 1 mm, 0.9 mm, 0.8 mm, 0.7 mm, 0.6 mm or 0.5 mm. In one embodiment, the circumferential grooves have a depth of about 0.2 to 1.0 mm. In one embodiment, the circumferential grooves have a depth of about 0.3 to 0.7 mm, or 0.3 to 0.6 mm.

In one embodiment, the or each distal aperture is disposed in the conical end portion of the distal scraping portion, typically proximal of the scraping formation(s).

In one embodiment, the sampling device and reaction chamber are configured for secure engagement. In one embodiment, the sampling device and reaction chamber are configured for sealing engagement, typically by means of a sealing friction fit. In one embodiment, the sampling device and reaction chamber are configured for snap-fit mounting together.

In one embodiment, the sampling kit includes a plurality of sampling devices. In one embodiment, each of the plurality of sampling devices are detachably mounted in a well of a multiwell plate.

In one embodiment, the multiwell plate includes an electronically identifiable tag. The tag may be, for example, an RFID tag or a barcode.

In another aspect, the invention provides a sampling device having a proximal handling portion and a distal scraping portion comprising a plurality of scraping formations configured to collect a sample of tissue when the distal scraping portion is rubbed against a surface of the tissue, wherein the distal scraping portion comprises a conical end portion and the scraping formations comprises one or more fully or partially circumferential edges having a depth of not more than 1 mm.

In one embodiment, the circumferential edges are provided by grooves. In another embodiment, the circumferential edges are provided by steps.

In one embodiment, the circumferential edges have a depth of not more than 1 mm, 0.9 mm, 0.8 mm, 0.7 mm, 0.6 mm or 0.5 mm.

In one embodiment, the circumferential edges have a depth of about 0.3 to 1.0 mm. In one embodiment, the circumferential grooves have a depth of about 0.3 to 0.7 mm, or 0.3 to 0.6 mm.

In another aspect, the invention provides a method of sampling and treating tissue comprising the steps of:

providing a sampling kit comprising a reaction chamber and a sampling device configured for detachably mounting in the reaction chamber and providing a reaction volume defined between the base of the reaction chamber and the sampling device, the sampling device having a proximal handling portion and a distal scraping portion comprising a scraping formation configured to collect a sample of tissue when the distal scraping portion is rubbed against a surface of the tissue;

performing a tissue sampling operation by scraping the distal scraping portion of the sampling device against the tissue whereby a sample of the tissue is collected by the scraping formation;

detachably mounting the tissue sampling device in the reaction chamber, characterised in that the method includes the steps of:

adding reaction liquid to the reaction volume through an internal lumen configured for the supply of reaction liquid from a distal end of the tissue sampling device to the reaction volume via a distal aperture disposed in the distal scraping portion when the sampling device is mounted in the reaction chamber, whereby the reaction liquid comes into contact with the sample of tissue to provide a reaction mixture in the reaction volume; and incubating the reaction mixture for a suitable period of time.

Generally, the step of adding reaction liquid comprises adding sufficient liquid to at least partially, and generally fully, immerse the distal aperture. This means that the liquid in the reaction chamber extends into at least the bottom of the internal lumen, allowing the liquid to be removed using a pipette inserted into the internal lumen. In one embodiment, reaction liquid formulated for cell lysis is added to the reaction chamber through the sampling device, where it mixes with the tissue sample causing lysis of cells releasing cellular DNA, which diffuses throughout the fluid including diffusing into the fluid contained in the internal lumen of the sampling device, allowing it to be removed through the internal lumen.

In one embodiment, the method includes a step of withdrawing an aliquot of the reaction mixture or a product produced by the reaction mixture.

In one embodiment, the reaction chamber comprises a cap for the tissue sampling device, in which the method includes a step of placing the cap, with the tissue sampling device mounted in the cap, in a well of a multiwell plate, prior to adding reaction liquid to the reaction volume.

In one embodiment, the cap is configured to detachably attach to the proximal handling end of the tissue sampling device to provide a handling extension, and in which the method includes a step of attaching the cap to the proximal handling end of the tissue sampling device prior to the tissue sampling operation, and detaching the cap from the proximal handing end after the sampling operation.

In one embodiment, the reaction chamber comprises a well of a multiwell plate, and in which the method includes a step of detachably mounting the tissue sampling device in the well of the multiwell plate after the sampling operation.

In another aspect, the invention relates to the sampling device alone.

In one embodiment, the sampling device has a proximal handling portion and a distal scraping portion comprising a plurality of scraping formations configured to collect a sample of tissue when the distal scraping portion is rubbed against a surface of the tissue.

The distal scraping portion comprises a conical end portion and the scraping formations comprises one or more fully or partially circumferential edges having a depth of not more than 1 mm.

In one embodiment, the circumferential edges are provided by grooves.

In one embodiment, the circumferential edges have a depth of not more than 0.5 mm.

In one embodiment, the circumferential edges have a depth of about 0.3 to 0.7 mm.

In yet another aspect, the invention provides system for high throughput sampling and indexing of multiple tissue samples, for example carcasses, comprising:

a multiwell plate having a plurality of wells;

a plurality of sampling devices nested in the wells of the multiwell plate, each sampling device having a proximal handling portion and a distal scraping portion nested in the well;

a robotic system comprising a robotic arm configured to engage a proximal handling portion of a first tissue sampling device while it is seated in a first well of a multiwell plate, lift the first tissue sampling device out of the first well, move the first tissue sampling device towards a first tissue sample and scrape the distal scraping portion against the first tissue sample, and replace the distal scraping portion of the sampling device in the first well;

a sensor for detecting an electronic ID from an electronic identification tag disposed on the first tissue sample;

a processor operably coupled to the robotic system and sensor and configured to receive the detected electronic ID from the sensor and assign the electronic ID detected for the tissue sample with the multiwell plate and first well identification; and a display system for displaying the tissue sample ID and associated plate and first well identification.

Typically, the tissue sample is a carcass, for example a meat carcass for use in the food industry.

In one embodiment, the multiwell plate and plurality of tissue sampling devices form part of a tissue sampling kit according to the invention.

In one embodiment, the system is configured for sampling multiple tissue samples (i.e., multiple carcasses) using multiple tissue sampling devices and optionally multiple multiwell plates and assigning a plate and well identification for each tissue sample sampled.

In one embodiment, the system comprises a liquid handling robot configured to simultaneously aliquot reaction fluid into a plurality of wells of a multiwell plate. In one embodiment, the system comprises a liquid handling robot configured to simultaneously withdraw an aliquot of a reaction mixture or a product produced by the reaction mixture from the plurality of wells of the multiwell plate.

Other aspects and preferred embodiments of the invention are defined and described in the other claims set out below.

BRIEF DESCRIPTION OF THE FIGURES

FIG. 6A shows the tissue sampling kit of FIG. 4 scraping against a surface of a meat carcass to sample tissue from the surface;

FIG. 6B shows the cap removed from the distal handle portion of the device and mounted on the proximal tissue scraping portion of the device;

FIG. 6C shows the assembly of FIG. 6B nested upright in a well of a multiwell plate;

FIG. 6D shows reaction fluid being pipetted into the reaction chamber through the internal lumen of the tissue sampling device;

FIG. 6E shows liquid being withdrawn from the reaction chamber through the internal lumen in the tissue sampling device

FIG. 7A shows the tissue sampling device of FIG. 1 scraping against a surface of a meat carcass to sample tissue from the surface;

FIG. 7B shows the tissue sampling device of FIG. 1 nested upright in a well of a multiwell plate;

FIG. 7C shows reaction fluid being pipetted into the well of the multiwell plate through the internal lumen of the tissue sampling device;

FIG. 7D shows liquid being withdrawn from the reaction chamber through the internal lumen in the tissue sampling device.

DETAILED DESCRIPTION OF THE INVENTION

Figures 1, 2, 3A, 3B:
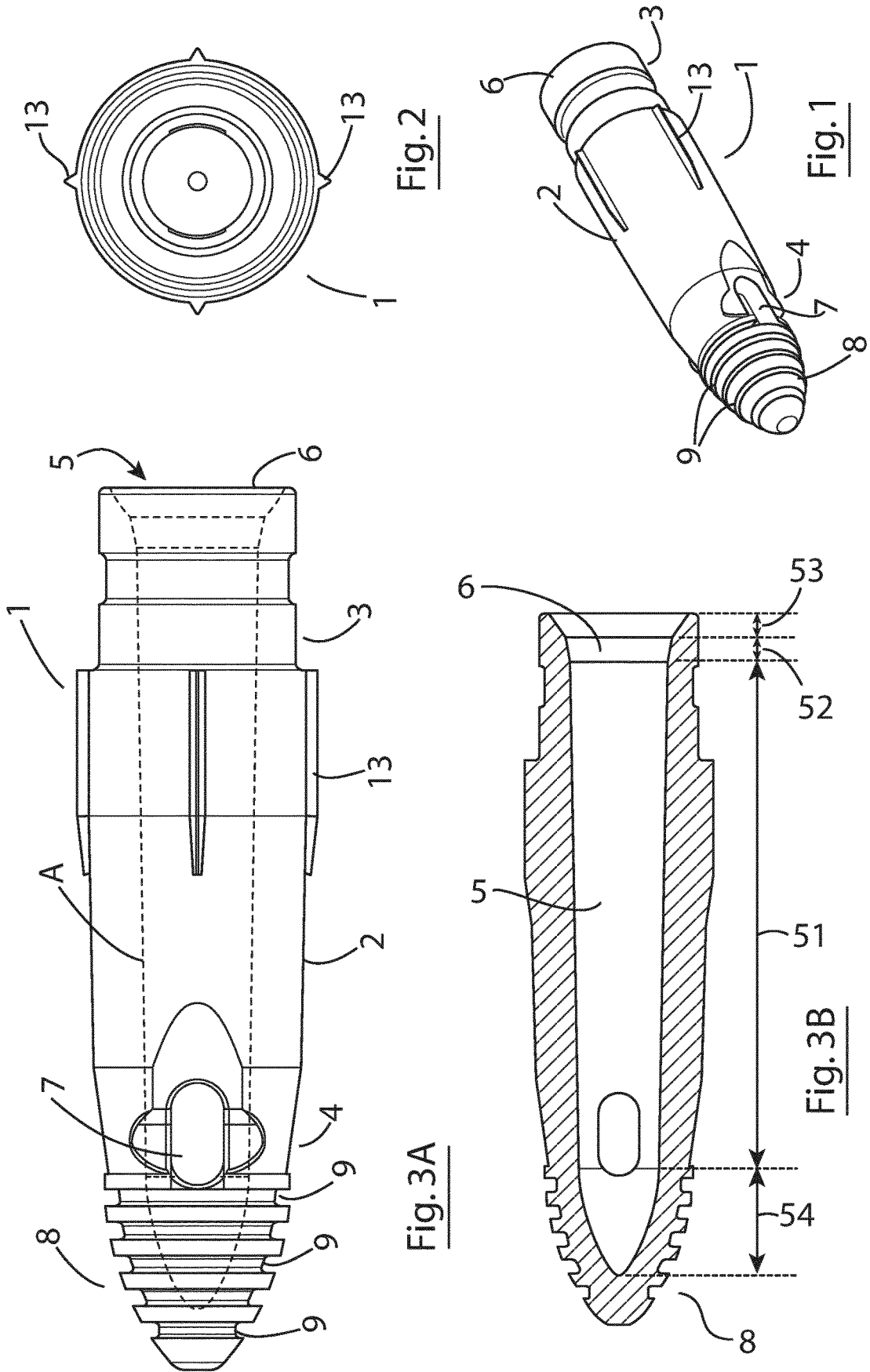
FIG. 1 is a perspective view of a sampling device according to the invention. This sampling device uses a well of a multiwell plate as a reaction chamber, and is suitable for use with an automated sampling system (i.e. a sampling robot).
FIG. 2 is an end view of the sampling device of FIG. 1 looking towards the handling portion of the device.
FIG. 3A is a side elevational view of the sampling device of FIG. 1 with the internal lumen shown in broken lines.
FIG. 3B is a cross-sectional view of the sampling device of FIG. 1.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "tissue" refers to any biological tissue, especially meat used in the food industry such as beef, poultry, lamb, pork, game, horse carcasses or parts thereof.

As used herein, the term "reaction fluid" refers to a liquid used to interact with the tissue sample and cause a reaction. Generally the reaction liquid is a reagent for cell lysis. Such reagents are described in Islam et al (Micromachines 2017 Mar. 8(3):83).

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to the drawings, and initially to FIGS. 1 to 3B, there is illustrated a first embodiment of a sampling device forming part of a sampling kit according to the invention and indicated generally by the reference numeral 1. This embodiment of the sampling device is for use with a well of a multiwell plate as a reaction chamber (as illustrated below in FIGS. 7 and 8) and is suitable for use with an automated sampling system described below. The device comprises an elongated bullet-shaped body 2 having a proximal handle portion 3 and a distal tissue scraping portion 4. The device is hollow having an internal lumen 5 providing fluid communication between an open top 6 and one or more apertures 7, for example two apertures disposed on opposite sidewalls of the distal tissue scraping portion 4. The internal lumen is illustrated in broken lines A in FIG. 3A.

A distal end 8 of the device includes a scraping formation 9, which provide scraping edges configured to collect tissue fibres when the scraping distal portion is scraped against a carcass.

For example, the scraping formation 9 comprises a series of five circumferential grooves spaced along the length of the distal tissue scraping portion 4, and located between the extremity of the device (distal end 8) and the aperture(s) 7 of the scraping portion 4.

A higher number of grooves (for example between six and ten grooves) can be used to increase the amount of collected tissue samples.

A lower number of grooves (for example between one and four grooves) can be used to reduce the size of the tissue scraping portion 4.

In particular, the scraping formation 9 and apertures 7 can be adapted to ensure that some reaction liquid mixed with the tissue sample extends into the bottom of the internal lumen and can be removed through the lumen. The amount of reaction liquid that can be inserted through the internal lumen can also be adapted.

A number of five grooves is thus a good compromise between the amount of collected tissue samples and size of the tissue scraping portion 4.

For example, the circumferential grooves can have a width of about 0.5 mm to about 0.7 mm. The crest between two grooves can have a width of about 0.5 mm to about 0.7 mm.

As an example, the first groove (located proximal to the extremity of the device) has a width of 0.55 mm, the other grooves have a width of 0.6 mm, the crest between two grooves has a width of 0.55 mm, and the crest/rim between the upper groove (fifth groove located proximal to the aperture 7) and the rest of the sampling device has a width of 0.50 mm.

The circumferential grooves can have a depth of about 0.3 mm to about 0.5 mm.

These dimensions have been found to be effective at removing a sufficient amount of tissue fibres from a meat carcass without tearing or ripping tissue from the carcass, irrespective of the amount of force used during the sampling operation, and without compromising the geometrical strength of the sampling device (which is substantially hollow).

In another embodiment, the scraping formation 9 comprises a helical groove or thread.

For example, as illustrated in FIG. 3B, the internal lumen 5 of the sampling device can have a main section 51 in the shape of a cylinder with, for example, a 1° draft angle. The lumen extends from the top aperture/opening 6 to the distal scraping portion 8 of the device. The diameter of the cylinder at the top aperture can be about 4 to 6 mm, for example 4.17 mm. The diameter of the cylinder at the bottom end can be about 3 to 4 mm, for example 3.42 mm.

The draft angle of the internal lumen can be used to create a friction fit between the sampling device and a gripper pin of a robotic end-of-arm-tool (EOAT) such as disclosed below. In this way, the sampling device can be handled even in an unattended configuration, for example in an abattoir/slaughterhouse. In particular, such draft angle helps to ensure effective robotic operation every time EOAT engages the sampling device while removing and inserting in a well of a multiwell plate, during the tissue sampling process.

The internal lumen 5 of the sampling device can also have one or more sections in the shape of a truncated cone at the top aperture/opening 6. In the example illustrated in FIG. 3B, the internal lumen 5 of the sampling device has a first section 52 in the shape of a first truncated cone and a second section 53 in the shape of a second truncated cone, the smallest diameter of the second truncated cone being the largest diameter of the first truncated cone, for example 4.59 mm, and the smallest diameter of the first truncated cone being the largest diameter of the cylinder, for example 4.17 mm.

The internal lumen 5 of the sampling device can also have an end section 54 at the distal scraping portion 4, that can match the shape of the scraping portion 4. For example, the distal scraping portion of the device is generally parabolic, and the end section 54 of the internal lumen 5 is a parabolical end section.

As already mentioned, the internal lumen 5 comprises at least one aperture 7.

According to a particular embodiment, at least one of said apertures 7 is located in a sidewall of the distal scraping portion. For example, two apertures are provided in the opposite sidewalls of the distal scarping portion.

In one embodiment, the internal lumen 5 comprises at least one aperture located above the scraping formation, not on the scraping formation. For example, such aperture(s) can be positioned proximate to the scraping formation, at less than 2 mm, and preferably less than 1 mm, from the upper groove of the scraping portion. In one embodiment, such aperture(s) can be in fluid communication with the upper groove of the scraping portion.

Such location of said at least one aperture not on the scraping formation avoid blockage of the aperture(s) with the tissue samples while collecting a sample of tissue by scraping the surface of the tissue (for example the carcass of an animal). According to at least one embodiment, such location also avoids blockage of the pipette/needle when a pipette/needle is used for removing liquid through the lumen.

According to at least one embodiment, such location of said at least one aperture proximal to the scraping formation allows the aperture(s) to be fully submerged in the diffused reaction fluid (for example reaction liquid for cell lysis mixed with the tissue sample cells releasing cellular DNA) of the reaction chamber. In this way, the diffused reaction fluid extends into at least the bottom of the internal lumen, allowing the diffused reaction fluid to be removed using for example a pipette inserted into the internal lumen.

In one embodiment, the distal scraping portion of the device is generally parabolic. In this way, at least one aperture located in the distal scraping portion is not blocked by a wall of the reaction chamber when the sampling device is inserted in the reaction chamber.

Several apertures can be provided.

A low number of apertures (for example one or two) is sufficient to insert and remove liquid from the reaction chamber. For example, one aperture can be provided at the bottom end of the distal scraping portion and one or more apertures can be provided in a sidewall of the distal scarping portion. In another example, several apertures can be provided in a sidewall of the distal scarping portion. The distance between the bottom end of the distal scraping portion and each aperture can be different.

A higher number of apertures (for example three to five) can also be provided, for example to improve the distribution of liquid in the reaction chamber.

The aperture(s) are designed to be large enough to allow aqueous liquids to drain freely out of the aperture(s), for example under gravity. An aperture can have, for example, a ring shape (with a diameter of about 1 mm to 4 mm), a square shape (with a dimension of about 1 mm to 4 mm), an oblong shape (with a length of about 3 to 4 mm, for example 3.50 mm, and a width of about 1 to 2 mm, for example 1.75 mm), a rectangular shape, etc.

When several apertures are provided, each aperture can have a different shape.

An aperture of less than 1 mm (diameter or length) may resist free-flow of liquid. An aperture of more than 4 mm (diameter or length) may compromise the structural integrity of the device.

In the example illustrated in FIG. 3B, the aperture(s) has (have) an oblong shape, and is (are) located at the bottom end of the main section 51 in the shape of a cylinder. The length of an aperture can be of about 3 to 4 mm, for example 3.50 mm, and the width can be of about 1 to 2 mm, for example 1.75 mm.

According to a particular embodiment, the through lumen 5 configuration allows a pipette, syringe needle, or any suitable device that can be used for withdrawing liquid out of the reaction volume or pushing liquid into the reaction volume to be inserted into the lumen and, in particular, extend through it into the reaction volume (for example parabolic end section 54).

This helps in the supply and withdrawal of liquid without having to remove the sampling device from the well or the cap, at any stage, thereby reducing the risk of cross-contamination.

Such pipette can be for example a Biomek™ tip of 230 μL from Beckman Coulter™ (reference B85903) or a EZ-Load™ pipette tip of 125 μL from Apricot Designs™, or any suitable pipette, for example any standard pipette.

It thus also enables use of standard liquid handling robots, such as for example the Beckman Coulter i7™, or any liquid handling machine that can deal with multiwell plates standardized for example by the "Society for Biomolecular Sciences" (SBS), such as the Apricot Personal Pipettor™.

According to one embodiment, the proximal handle portion 3 includes ribs 13. Such ribs or external "fins" can be provided at the proximal handle portion 3 to allow air to exit from the well, and thus facilitate the free flow of the reaction liquid through the lumen and exit via the aperture(s) 7, while the sampling device is inserted into the well. They serve to provide both breather ventilation and friction fit of the sampling device in the well. They can also facilitate secure and snug mounting of the device in a reaction chamber.

The sampling device can be made of plastic, to be easily manufactured by injection moulding. It can be made as a one-piece of plastic.

For example, it can be made of polypropylene or any material suitable for lab processing (such as liquid fluid dynamics for automatic dispense and withdrawal, sterilization etc), as well as for safe robotic operations while scraping the tissue.

In a particular embodiment, the sampling device is made of polypropylene polymer material such as RP373R material, i.e. polypropylene random copolymer. Such material is mainly used for applications in the pharmaceutical, medical device, laboratory and diagnostics area.

In the first embodiment, the kit of the invention comprises the sampling device 1 described above and a well of a multiwell plate as a reaction chamber into which the sampling device is securely mounted after a tissue sampling operation with the distal scraping portion of the device nested in the base of the well. The well of the multiwell plate and scraping section of the device 1 are dimensioned to provide a reaction volume defined between the device and the wall of the well for receipt of a reaction fluid. This is illustrated in more detail in FIG. 8 which shows the device 1 nested in the well 20 of a multiwell plate 21 and showing the reaction volume 16 defined by the well 20 and device 1 which is filled with reaction fluid 17 up to above the level of the aperture 7 to a height H.

Figures 4A, 4B, 5:
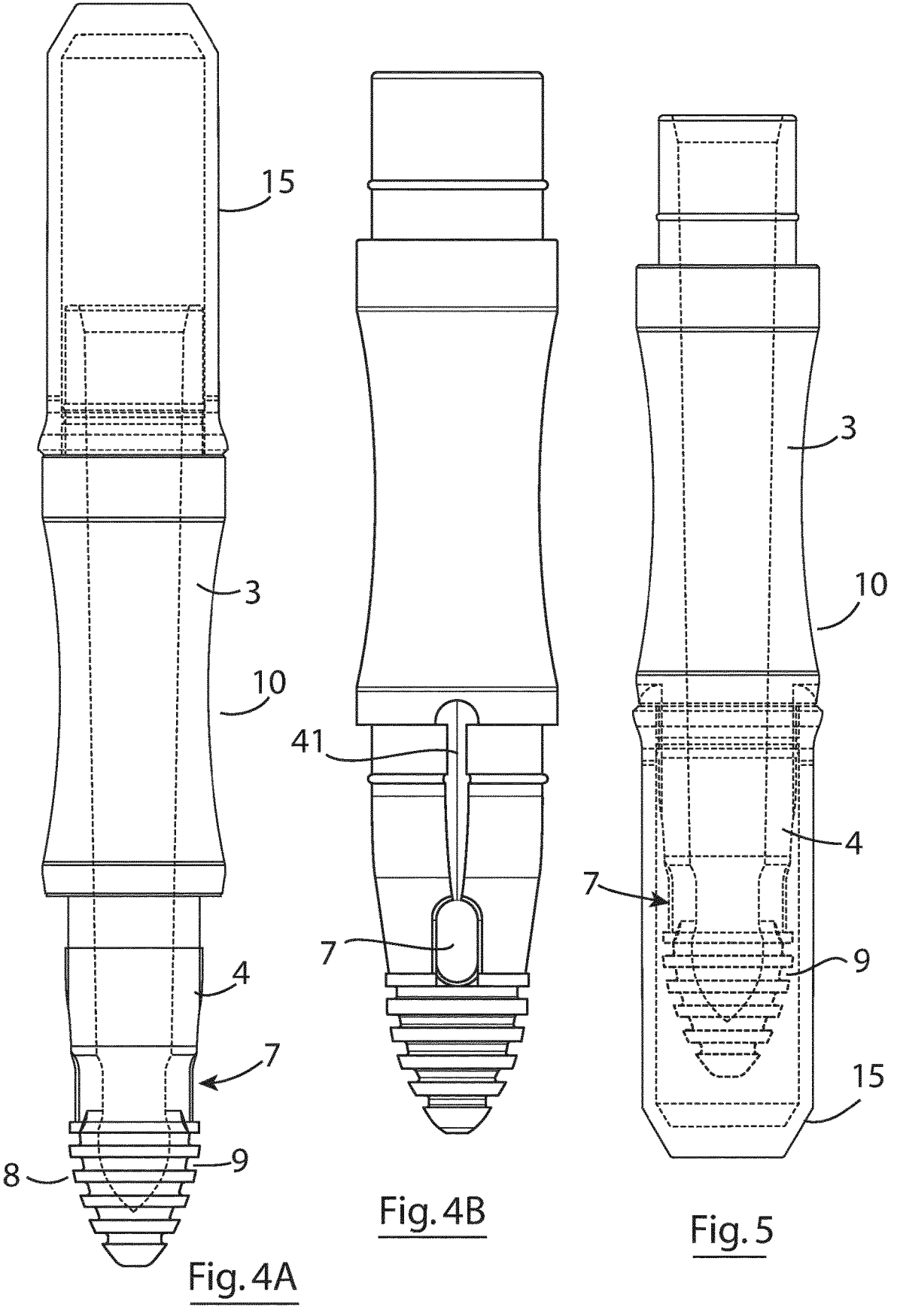
FIGS. 4A, 4B and 5 are elevational views of a sampling kit according to the invention comprising a sampling device and a detachable cap for the sampling device that functions as a handle extension in a first configuration (FIG. 4A and FIG. 4B) and a reaction chamber in a second configuration (FIG. 5). This embodiment of the invention is suitable for manual (non-automated) use.

Referring to FIGS. 4A, 4B and 5, a sampling kit according to an alternative embodiment of the invention is illustrated. This embodiment of the sampling device is for use with a cap as a reaction chamber and is also suitable for manual (non-automated) use. The kit comprises the sampling device 1 or an alternative sampling device 10 (which is broadly similar to the device 1 but has a longer proximal handle portion 3) and a cap 15 that functions as a reaction chamber.

In a first configuration of the kit (FIGS. 4A and 4B), the cap 15 is detachably attached to the tissue handling portion 3 of the device 10 providing a handle extension for use during a tissue sampling operation. In a second configuration, employed after a tissue sampling operation, the cap 15 is attached to the distal scraping portion 4 of the device 10 where it acts as a reaction chamber.

According to one embodiment, the sampling device 10 comprises at least one slot 41. Such slot(s) is(are) located above the aperture(s) 7, for example on an upper part of the distal scraping portion. It ensures an air connection between the reaction chamber and the exterior of the sampling device, when the cap is attached to the distal scraping portion 4 of the device 10, and thus serves to provide ventilation of the sampling device.

It can be noted that either the sampling device 1 or the alternative sampling device 10 are suitable for use with an automated sampling system described below.

Referring to FIGS. 6A-6E and 7A-7D, the use of the two embodiments of the kit of the invention are illustrated. In the first embodiment (FIGS. 7A-7D), the use of the device and kit of FIGS. 1 to 3B is illustrated, where the reaction chamber is provided by the well of a multiwell plate. In the second embodiment (FIGS. 6A-6E), the use of the kit of FIGS. 4 and 5 is illustrated, where the reaction chamber is provided by a cap 15.

Figures 6A, 6B, 6C, 6D, 6E:
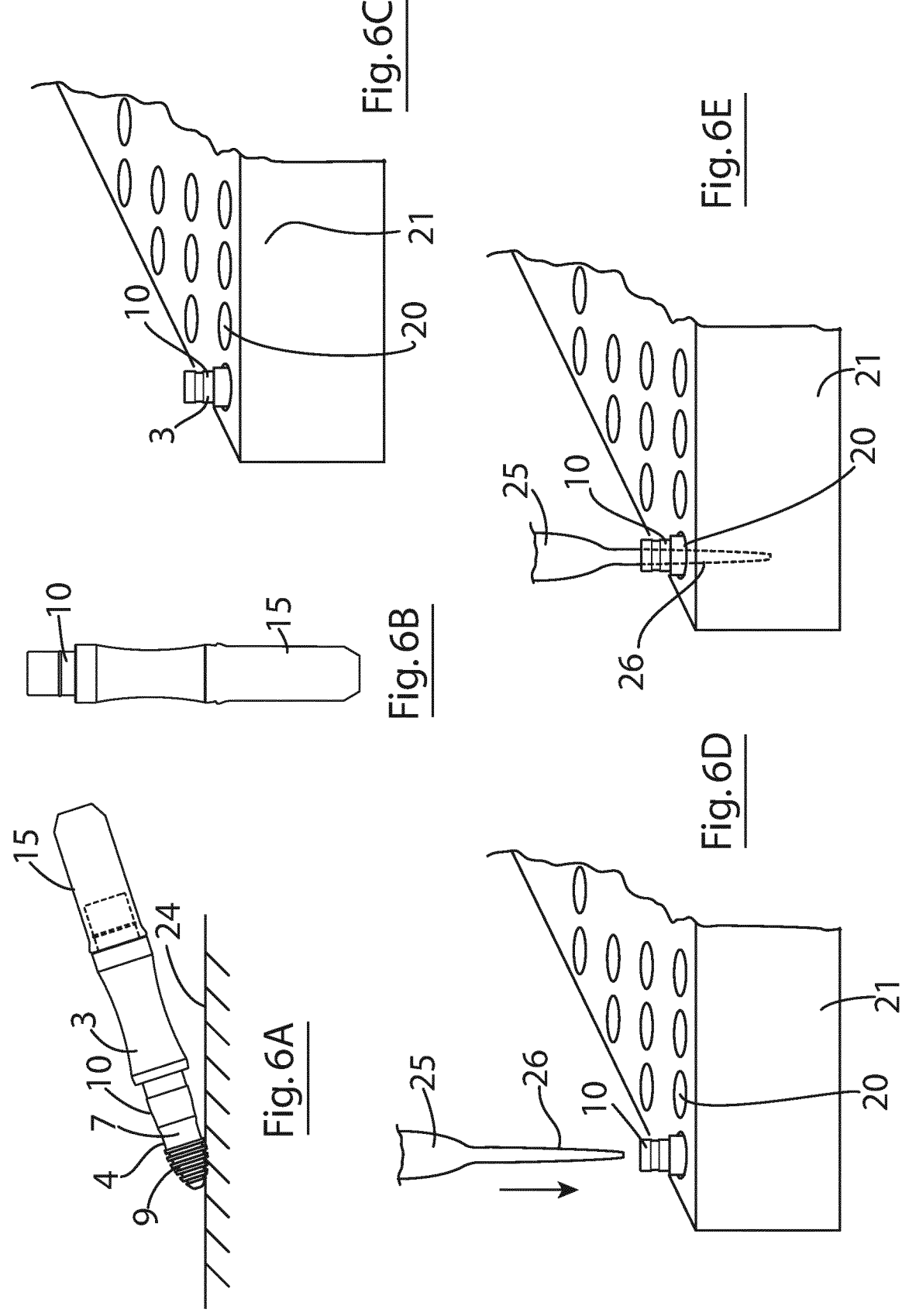
FIG. 6A to 6E illustrate a tissue sampling and treatment process of the invention that employs the sampling kit of FIGS. 4A, 4B and 5 (in which the reaction chamber is provided by a cap)

Referring specifically to FIG. 6A, the sampling device 10 and cap 15 attached to a proximal handling end of the device are shown sampling tissue from a surface of a carcass 24. The user holds the cap 15 and scrapes the conical end and grooves 9 along the surface of the carcass or substrate where the shallow grooves dislodge and pick up some meat fibres without tearing or ripping chunks of tissue from the meat.

Referring to FIG. 6B, the cap 15 is then carefully detached from the proximal handling end of the device 10 and attached to the distal scraping portion 4 of the device, where it serves as a reaction chamber for cell lysis treatment of the tissue fibres.

Referring to FIG. 6C, the assembly is mounted, cap first, in a well 20 of a multiwell plate 21 for storage until further analysis.

Referring to FIG. 6D, a pipette 25 with a pipette tip 26 is used to deliver reaction fluid to the reaction chamber in the cap 15 through the internal lumen in the device 10 without having to detach the device from the cap 15. Once the reaction liquid is delivered, it will mix with the tissue fibres and lyse the cells in the fibres, releasing DNA from the cells which will diffuse around the reaction fluid including reaction fluid in the internal lumen.

Referring to FIG. 6E, the pipette 25 with pipette tip 26 (shown partly in broken lines) may then be used to withdraw some of the DNA-containing fluid in the internal lumen, again without having to demount the device 10 from the cap 15.

Figures 7A, 7B, 7C, 7D:
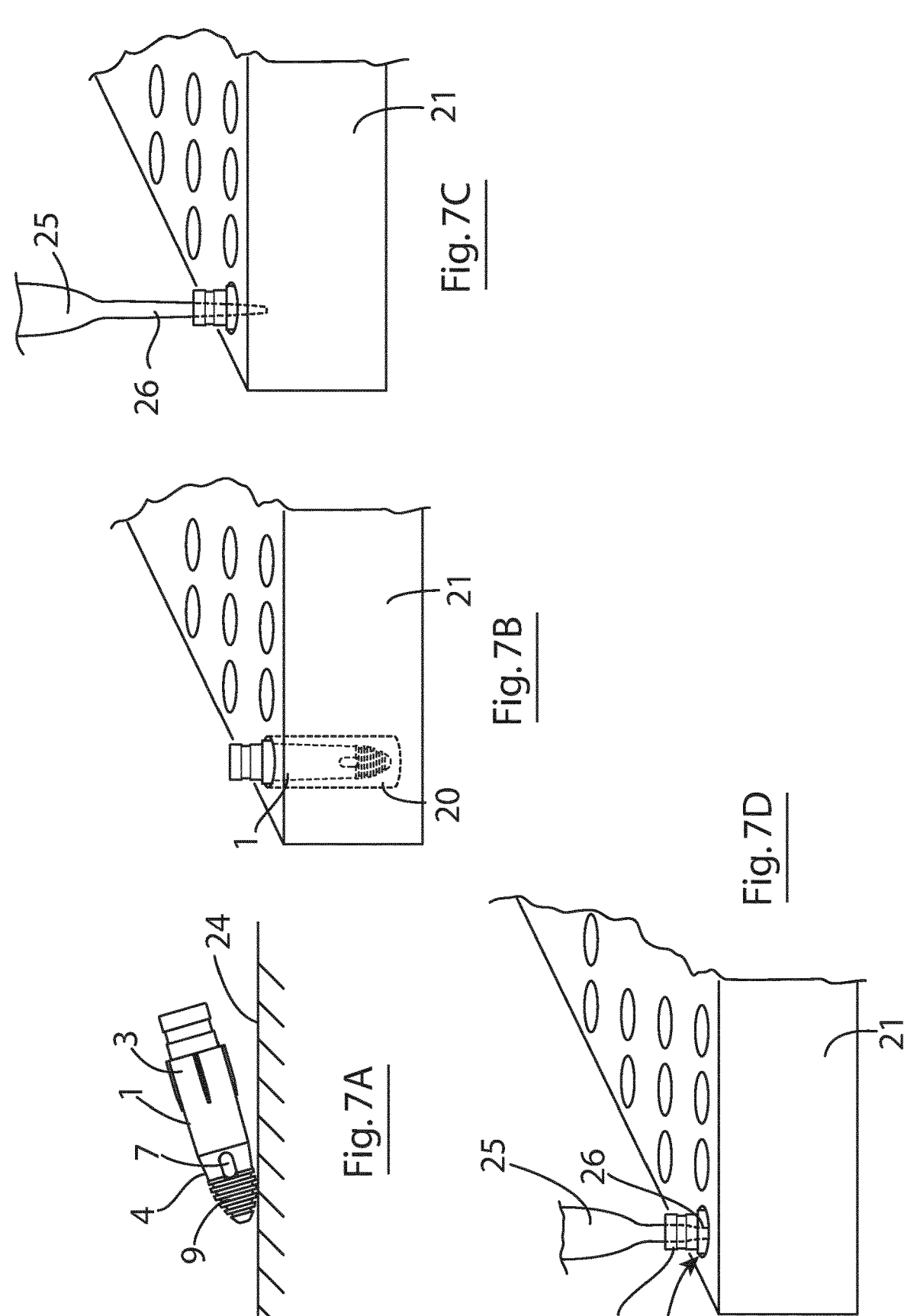
FIG. 7A to 7D illustrate a tissue sampling and treatment process according to an alternative embodiment of the invention that employs the sampling device of FIGS. 1 to 3B (in which a well of a multiwell plate is employed as a reaction chamber)

Referring specifically to FIG. 7A, the use of the first embodiment of the kit of the invention is illustrated in which parts identified previously are assigned the same reference numerals. In this embodiment, the sampling device 1 is shown sampling tissue from a surface of a carcass 24, where the user (or a robotic arm) holds the device 1 at the proximal handling portion 3 and scrapes the parabolic end with grooves 9 along the surface at an oblique angle to dislodge and pick up meat fibres.

Referring to FIG. 7B, the distal scraping portion of the device 1 is detachably mounted in a well 20 of a multiwell plate 21, which then serves as a reaction chamber for cell lysis treatment of the tissue fibres. The distal end of the device is shown in broken lines to illustrate the reaction volume defined by the device and the well.

Figure 8:
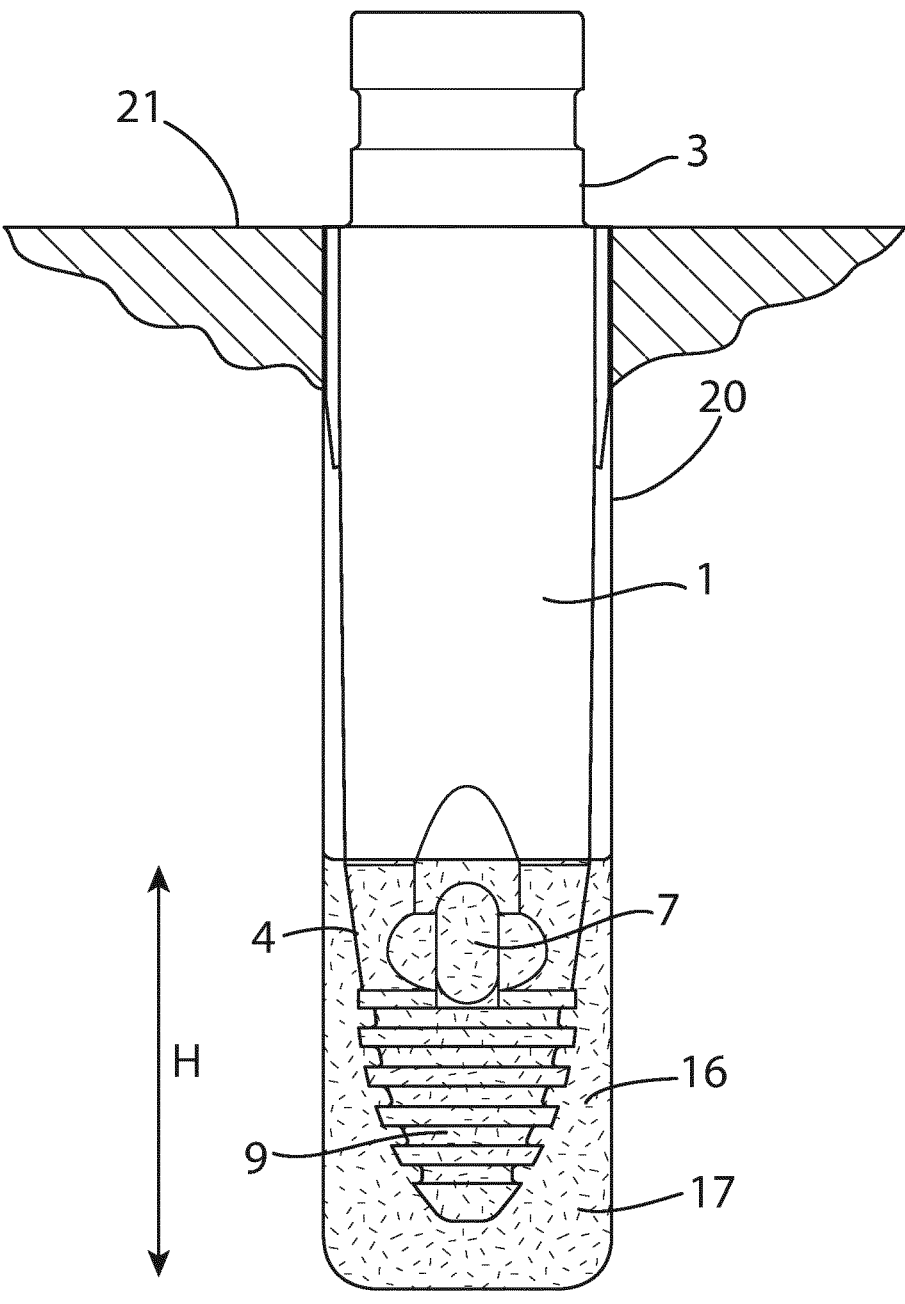
FIG. 8 is a sectional view of a sampling device of FIGS. 1 to 3B nested in a well of a multiwell plate with a reaction volume defined between the base of the well and the sampling device, and reaction fluid added to the well to a height H submerging the apertures in the device.

Referring to FIG. 7C, a pipette 25 with a pipette tip 26 is used to deliver reaction fluid to the reaction chamber in the well 20 of the multiwell plate 21 through the internal lumen in the tissue sampling device 1 without having to remove the device 1 from the well 20. Once the reaction liquid is delivered, it will mix with the tissue fibres and lyse the cells in the fibres, releasing DNA from the cells which will diffuse around the reaction fluid including reaction fluid disposed in the internal lumen. FIG. 8 illustrates in more details the device 1 in the well of the multiwell plate after reaction fluid has been added to the well.

Referring to FIG. 7D, the pipette 25 may then be used to withdraw some of the DNA-containing fluid in the internal lumen, again without having to remove the device from the well.

The device and kit of the invention allow tissue to be sampled and then treated (i.e. for cell lysis) in a reaction chamber (i.e. a detachable cap, or a well of a multiwell plate) without having to remove the tissue sampling device from the reaction chamber. As mentioned above, this obviates the problem associated with the prior art devices, which have to be removed from the well prior to addition of the reaction liquid, causing drips to fall on the plate and other wells leading to contamination problems. A further advantage is the use of the device with a series of shallow circumferential grooves, which has been found to normalise the amount of tissue removed from a carcass, irrespective of whether the scraping action uses too much or too little pressure.

Figure 9:
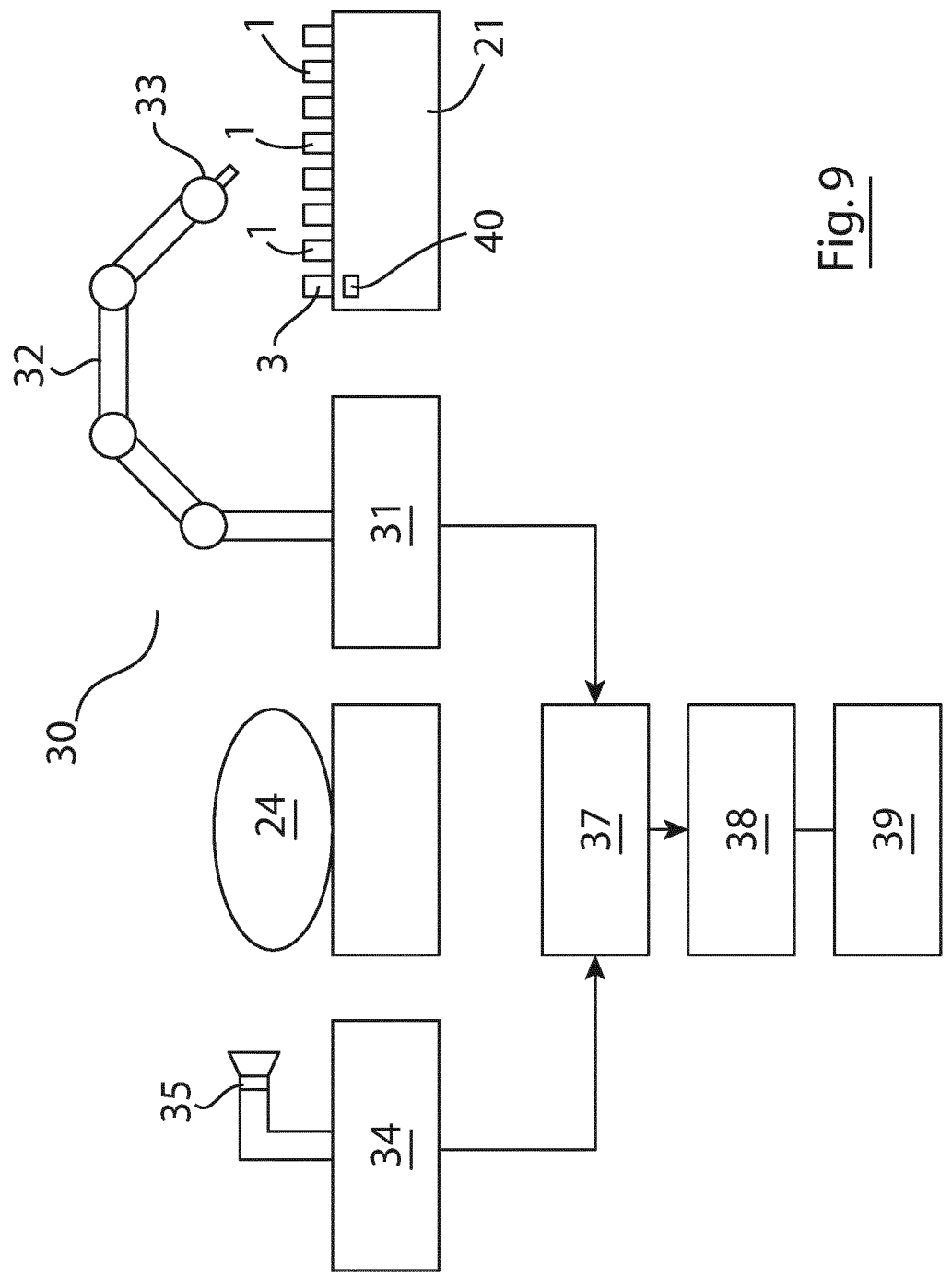
FIG. 9 is an illustration of an automated high-throughput carcass tissue sampling and indexing system according to the invention that employs the sampling kit illustrated in FIGS. 1 to 3B and 8.

Referring to FIG. 9, an automated robotic system 30 for high throughput sampling and indexing of multiple carcasses 24 is described. In this embodiment, the system comprises a multiwell plate 21 having a plurality of wells and a unique barcode 40, and a plurality of tissue sampling devices 1 nested in the wells of the multiwell plate 21, each tissue sampling device having a proximal handling portion 3 and a distal scraping portion 4.

A robotic sampling system 31 is provided and comprises a robotic arm 32 with an end of arm tool 33 configured to engage the inside of the proximal handling portion of a tissue sampling device while it is seated in well of a multiwell plate. The robotic arm is configured to lift the tissue sampling device out of the well, move the tissue sampling device towards a carcass and scrape the distal scraping portion against the carcass, and replace the tissue sampling device in the same well. The sampling system includes means for referencing the position of the plate with respect to the arm, allowing the system to direct to arm to the first well on the plate, and thereafter to the second, third, fourth wells, and to record the position of the well from which particular device has been removed.

The system includes a first sensor 34 including a camera 35 for identifying for detecting an electronic ID on the carcass 24. The system also includes a second sensor for detecting a barcode on the multiwell plate. The system also includes a processor 37 operably coupled to the robotic system 31 and the sensors and configured to receive the detected electronic ID of the carcass, the barcode of the multiwell plate, and the location of the well on the plate from which the sampling device has been removed. The processor is configured to assign the electronic ID of the carcass to a specific sampling device using a reference from the respective carcass ID and the reference location of the well on a multiwell plate 21 and the multiwell plate barcode 40. All the data is logged in to the computer data sheet with a datetime stamp.

The system generally also includes a display system 38 for displaying data comprising the carcass ID linked with the sampling device with reference to a well location on associated plate; and optionally, a communication system 39 for transmitting the data to a remote location via a communications system such as the internet.

The system may be employed to collect tissue samples from multiple carcasses at an abattoir, for example up to 10,000 a day, which samples are stored in wells of a number of 96-well plates. The system provides data comprising ID's for the carcasses samples and for each carcass data relating to the specific well and plate in which the tissue sample from that carcass is stored. The data may be displayed on paper using a printer or recorded on another medium such as a disk. The data may also be electronically transferred via a communication system to the lab where the samples are to be analysed.

Although not illustrated, the system may include a liquid handling robot configured to simultaneously aliquot reaction fluid into a plurality of wells of a multiwell plate, and simultaneously withdraw an aliquot of a reaction mixture or a product produced by the reaction mixture from the plurality of wells of the multiwell plate. The liquid handling robot part of the system is generally located in a different location to the robotic sampling system, for example in a laboratory. In one embodiment, the external base of each of the wells of the multiwell plate includes an electronic identification tag (for example a barcode) readable by a flat-bed scanner.

The liquid withdrawn from the reaction chamber is generally treated to profile or genotype the DNA or identify single nucleotide polymorphisms or other polymorphisms or haplotypes in the DNA. This may involve multiplex amplification of the DNA and next generation sequencing of all or part of the DNA. Methods and kits for high throughput or next generation sequencing are available, including Sequencing by synthesis (Illumina), Pyrosequencing (454), Ion semiconductor (Ion Torrent Sequencing) and Combinatorial probe anchor synthesis (cPAS-BGI-MGI). Targeted NGS is a next generation sequencing technique that focusses on amplicons and specific genes, and that employs amplification of the needed gene or amplicon by enzymatic amplification, which is then sequenced on a NGS platform. It is described in Bybee et al ("Targeted Amplicon Sequencing (TAS): A Scalable Next-Gen Approach to Multilocus, Multitaxa Phylogenetics". Genome Biology and Evolution. 3: 1312-1323. doi:10.1093/gbe/evr106. PMC 3236605) and Masser et al ("Targeted DNA Methylation Analysis by Next-generation Sequencing". Journal of Visualized Experiments. 96: 52488. doi:10.3791/52488. PMC 4354667). The liquid withdrawn from the chamber may be analysed to quantitatively or qualitatively detect other components from tissue, for example other nucleic acids or proteins.

Equivalents

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A sampling device configured for mounting in a reaction chamber providing a reaction volume defined between a base of the reaction chamber and the sampling device when the tissue sampling device is mounted in the reaction chamber, the sampling device comprising:

a proximal handling portion and;

a distal scraping portion comprising a scraping formation configured to collect a sample of tissue onto the scraping formation when the distal scraping formation is rubbed against a surface of the tissue, an internal lumen extending from an open top to at least one distal aperture in a sidewall of the distal scraping portion, said lumen being configured to supply reaction liquid from a distal end of the tissue sampling device to the reaction volume via the at least one distal aperture disposed in the sidewall of the distal scraping portion when the tissue sampling device is mounted in the reaction chamber.

2. The sampling device as claimed in claim 1, in which the sampling device is substantially hollow.

3. The sampling device as claimed in claim 1, including at least two distal apertures in the distal sampling portion.

4. The sampling device as claimed in claim 1, in which the distal aperture in the distal sampling portion is disposed proximally of the scraping formation.

5. The sampling device as claimed in claim 1, in which the internal lumen is configured to receive a pipette tip or a syringe needle.

6. The sampling device as claimed in claim 1, in which the distal scraping portion comprises a parabolical end.

7. The sampling device as claimed in claim 1, in which the scraping formation comprises one or more fully or partially circumferential grooves.

8. The sampling device as claimed in claim 7, in which the one or more fully or partially circumferential grooves has a depth of not more than 0.5 mm.

9. The sampling device as claimed in claim 1, wherein the scraping formation is configured to collect meat tissue fibres.

10. The sampling device as claimed in claim 1, wherein the sampling device is made as a one-piece of plastic.

11. The sampling device as claimed in claim 1, wherein the sampling device comprises an open proximal end and wherein the internal lumen is configured for the supply of reaction liquid from the open proximal end to the reaction volume.

12. A sampling device configured for mounting in a reaction chamber providing a reaction volume defined between a base of the reaction chamber and the sampling device when the tissue sampling device is mounted in the reaction chamber, the sampling device comprising:

a proximal handling portion and;

a distal scraping portion comprising a scraping formation configured to collect a sample of tissue onto the scraping formation when the distal scraping formation is rubbed against a surface of the tissue, said scraping formation comprising scraping edges configured to collect tissue fibers an internal lumen extending from a top to at least one distal aperture in a sidewall of the distal scraping portion, said lumen being configured to supply reaction liquid from a distal end of the tissue sampling device to the reaction volume via the at least one distal aperture disposed in the sidewall of the distal scraping portion when the tissue sampling device is mounted in the reaction chamber.

\* \* \* \* \*